United States Patent [19]
Roelofs et al.

[11] 3,952,093
[45] Apr. 20, 1976

[54] NOVEL ATTRACTANT COMPONENTS FOR MALES OF THE TOBACCO BUDWORM MOTH

[76] Inventors: Wendell L. Roelofs, 652 W. North St.; Ada S. Hill, 575 White Springs Road; Thomas C. Baker, 432 Castle St.; Ring T. Carde, Glass Factory, Bay Road, all of Geneva, N.Y. 14456

[22] Filed: Apr. 4, 1975

[21] Appl. No.: 565,310

Related U.S. Application Data

[62] Division of Ser. No. 460,633, April 12, 1974, Pat. No. 3,917,711.

[52] U.S. Cl. .................................................. 424/84
[51] Int. Cl.² ........................................... A01N 17/14
[58] Field of Search ...................................... 424/84

[56] References Cited
UNITED STATES PATENTS 3,866,349   2/1975   Meijer et al. .......................... 424/84

OTHER PUBLICATIONS

Science, Vol. 174, pp. 297–299, Oct. 1971.
Nature, Vol. 219, p. 513, Aug. 1968.
Nature, Vol. 224, p. 723, Nov. 1969.

Primary Examiner—Donald B. Moyer
Attorney, Agent, or Firm—Behr & Woodbridge

[57] ABSTRACT

Cis- 9-tetradecenal and cis-11-hexadecenal have been synthesized and found to be, in combination, sex attractants for males of the species *Heliothis virescens* (Tobacco Budworm Moth) and major economic pest. Methods of preparing said compounds and methods of utilizing said compounds as attracting agent are disclosed.

6 Claims, No Drawings

NOVEL ATTRACTANT COMPONENTS FOR MALES OF THE TOBACCO BUDWORM MOTH

RELATED APPLICATION

This is a division, of application Ser. No. 460,633, filed Apr. 12, 1974, now U.S. Pat. No. 3,917,711.

FIELD OF THE INVENTION

DESCRIPTION OF THE PRIOR ART

In recent years, the ecological problems raised by the wide-spread use of certain insecticides, in particular halogenated aromatics such as DDT, have initiated the search for more specific methods of destroying insect pests, which, if they do not entirely eliminate the use of such harmful insecticides as pesticides, at least considerably cut down the area in which they are broadcast. One mode which has been found of great interest in recent years has been the use of sex attractants or pheromones to attract either the male or the female of a particular species or a number of species to a particular and small location where they can be destroyed thereby interrupting the breeding cycle and cutting down the number of such pests in the next season. One technique employed for this purpose is to isolate either the male or the female pheromone and insert it into an insect trap which is then located in the area which it is desired to protect from a particular species of moth or other insect. The vapor from the trap attracts the insects into the trap where they are either held or killed, thus removing them from the general populace. Two problems have been associated with this approach. The first problem is that of availability. Enormous numbers of laboratory reared insects are required to produce the naturally occurring attractant. This clearly is not a commercially feasible approach and therefore the nature of attractants must be determined and such compounds prepared synthetically.

SUMMARY OF THE INVENTION

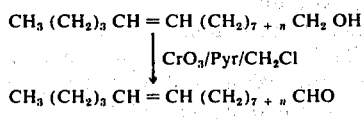

Where $n = 0$ or 2

The starting materials for the foregoing synthesis, namely cis-9-tetradecenol and cis-11-hexadecenol may be readily obtained by methods well known in the art.

It has been found that a combination of cis-9-tetradecenal and cis-11-hexadecenal provide a composition which has male attracting properties with respect towards males of the species *Heliothis virescens* (*Lepidoptera: Noctuidae*) (Tobacco Budworm). It has also been found that cis-11-hexadecenal per se has similar properties with respect to *Heliothis zea*.

The Tobacco Budworm is a major economic pest in the United States. Therefore, the finding of a male attractant compound for this insect is of great utility in providing ecologically desirable methods of reducing the population of this insect without the necessity of large scale spraying which is required at this time. The attractant compositions of the present invention may be utilized principally in two ways. The first by inserting an attractively effective amount in insect traps which are hung in locations infested with the insects. Alternatively, the compositions may be encapsulated in water insoluble, substantially vapor permeable micro capsules and distributed in the infested area. This distribution causes sexual disorientation in the males and thus substantially reduces the mating process without the necessity for the use of more expensive traps. The micro capsules may be distributed on the ground or compounded with substantially water insoluble adhesives and sprayed on plants in the affected areas. It has been found that in many cases it is merely necessary to spray barrier areas with these compositions rather than spraying the entire area to be protected.

DESCRIPTION OF THE PREFERRED EMBODIMENTS

There is disclosed herein a general method for the synthesis for cis-9-tetradecenal. The method is equally applicable to the synthesis cis-11-hexadecenal.

In the process of the first invention an oxidizing solution of chromium trioxide and pyridine in methyline chloride is prepared. It is desirable to utilize a molar ratio of about 2:1 between pyridine and chromium trioxide and a substantial excess of chromium trioxide over the alcohol to be oxidized. Suitably a molar ratio of from about 4 to about 8, suitably about 6, moles of chromium trioxide per mole of alcohol are employed. In the preferred modification of the procedure the cis-9-tetradecenal is taken up in a small amount of methylene chloride and added to the mixture of chromium trioxide in pyridine/methylene chloride. Reaction is rather rapid and should be considered complete in about fifteen minutes at ambient temperatures. The product is recovered by decantation of the solvent from a tarry precipitate followed by removal of the solvent under reduced pressure and extraction of the residue with petroleum ether. This extract is then washed with dilute aqueous mineral acid suitably hydrochloric acid, brine, and a mild base, suitably aqueous sodium bicarbonate then dried and evaporated to yield a residue which is then further purified. Suitably purification is carried out by chromatography, preferably on Florisil, in order to separate the desired aldehyde from the unreacted alcohol.

As stated hereinbefore, the starting alcohols may be either synthesized by known methods or purchased from commercial sources. The alcohols thus produced are not always totally isomerically pure. Isomerically pure material may be obtained by preparative scale thin layer chromatography of the corresponding acetates. These acetates are prepared from the corresponding alcohols by methods well known in the art; for example, by reaction of the alcohol with acetic anhydride in pyridine.

The acetates are then chromatographed suitably by a thin layer chromatography preferably preparative scale thin layer chromatography on silver nitrate impregnated silica gel. The recovered cis acetates are then saponified in the conventional manner and converted into the desired aldehydes in the manner set forth hereinabove.

The efficacy of the compounds produced in accordance with the present invention, with respect to its attractive activity upon males of the species *H. virescens* and *H. zea*, was tested both in laboratory bioassays and field tests. In a bioassay test a selected number of male moths of the species under test, say between six and twelve moths, usually about ten moths, were placed in a substantially air tight transparent cylinderical container which was equipped with an inflow and outflow point. A predetermined amount of the attractant composition under test is placed in the path of air inflow into the tank. Suitably this is done by placing said predetermined amount of attractant on a piece of filter paper and placing the filter paper in the path of the airflow.

The activity of the moths in the tank is measured prior to vapor injection. Air is then passed over the vapor source into the tank for about one minute and the number of moths flying during that time is noted. Where T equals total number of moths in tank, $F^1$ equals number of moths flying before vapor injection, $F^2$ equals number of moths flying during injection time.

The activity factor may be expressed as:

$$100 \times \frac{F^2 - F^1}{T - F^1}$$

A typical result for *H. virescens* and *H. zea* is shown below in Table 1:

TABLE I

Male Bioassay of *H. virescens* and *H. zea*

| Treatment | *H. virescens*[1] | *H. zea*[1] |
|---|---|---|
| (spontaneous activity) | 3.2 ± 1.1 | 3.9 ± 1.6 |
| 100 ng c11–16:Ald[2] | 19.3 ± 3.0 | 66.5 ± 7.5 |
| 30 ng c 9–14:Ald[3] | 7.5 ± 2.9 | 6.3 ± 4.3 |
| 100 ng c11–16:Ald + 30 ng c 9–14:Ald | 90.8 ± 4.9 | 32.2 ± 6.5 |

[1]Mean % response ± standard error
[2]cis-11-hexadecenal
[3]cis-9-tetradecenal

In a field test for *H. virescens* carried out in North Carolina (which is summarized in Table 2 below) it was found that attractivity was shown for a combination of cis-11-hexadecenal with cis-9-tetradecenal in ratios of from about 200:1 to about 2:2. It will be appreciated that the figures given represent charge amounts since the C14 aldehyde evaporates faster than the C16 aldehyde and these figures would not therefore represent the actual ratio of components in a test trap at a particular concentration.

TABLE II

Field Tests with Synthetic Compounds for *H. virescens* Attractancy

| TREATMENTS | | NUMBER OF MALES TRAPPED | | |
|---|---|---|---|---|
| c11–16:Ald[2] | c9–14:Ald[3] | TEST A | TEST B | Total |
| 1000 μg | 0μg | 0 | 0 | 0 |
| " | 2.5 | 0 | 0 | 0 |
| " | 5 | 10 | 0 | 10 |
| " | 7.5 | 6 | 0 | 6 |
| " | 15 | 1 | 2 | 3 |
| " | 30 | 3 | 4 | 7 |
| " | 40 | 16 | 10 | 26 |
| " | 50 | 0 | 1 | 1 |
| " | 75 | 2 | 4 | 6 |
| " | 100 | 11 | 6 | 17 |
| " | 150 | 5 | 0 | 5 |
| " | 200 | 17 | 8 | 25 |
| " | 300 | 7 | 4 | 11 |
| " | 500 | 0 | 2 | 2 |
| 500 | 500 | 0 | 0 | 0 |
| 250 | 500 | 0 | 0 | 0 |
| 100 | 500 | 0 | 0 | 0 |
| 50 | 500 | 0 | 0 | 0 |
| 0 | 500 | 0 | 0 | 0 |
| Unbaited | | 0 | 0 | 0 |

TABLE II-continued

Field Tests with Synthetic Compounds for *H. virescens* Attractancy

| TREATMENTS | | NUMBER OF MALES TRAPPED | | |
|---|---|---|---|---|
| c11–16:Ald[2] | c9–14:Ald[3] | TEST A | TEST B | Total |
| | | | | 119 |

[2]cis-11-hexadecenal
[3]cis-9-tetradecenal

In the field tests, Pherotrap insect traps (Zoecon Corp., Palo Alto, Ca.) were charged with the material under test and hung in fields where the moth was prevalent. The attractant was placed in these traps on rubber septa (5 × 9mm rubber stoppers, sleeve type, Arthur H. Thomas Co.).

The charge in the traps may lie in the range of 1 to 10,000 μg, suitably 500 to 1500 μg per trap of total attractant composition. The total charge depending on the mode of charging the trap.

The attractant substance may be used per se. In order to obtain more accurate dispensing of the attractant it may be taken up in a suitable volatile diluent. Any reaction inert volatile organic solvent may be employed. Lower alkanols such as methanol or ethanol ethers, such as diethyl ether, halogenated hydrocarbons such as methylene chloride and alkyl ketones such as acetone or the like may be employed.

These solvents will evaporate very rapidly leaving the attractant in the trap which may then volatilize slowly. Hence, the proportion of attractant to solvent is not important.

The rate of volatilization may be reduced by dissolving the attractant in a substantially non-odorous reaction inert viscous liquid. The nature of this viscous liquid is not critical, however, olive oil has been found suitable as an attractant keeper as have glycerol trioctanoate, mineral oil and Nujol. The use of such keepers permits the raising of dosage per trap to about 10,000 μg. This permits the traps to be active for a longer time without creating the repulsant effect noted with high concentrations of sex attractants.

It will be seen, therefore, that the preparation of compositions of the attractant, a keeper, and a diluent is most desirable. The concentration of the components is not critical as the determining factor is the amount dispensed per trap. Thus, where a 1 ml. sample comprising 10 mg. is to be dispensed per trap, a suitable composition would be as follows:

| cis-9-tetradecenal | 2.5 g. |
|---|---|
| cis-11-hexadecenal | 7.5 g. |
| Olive Oil | 100 ml. |
| Ethanol | 900 ml. |

It has also been found that breeding control may be exercised without the use of traps. The principle of this method depends upon the finding that if an area is substantially dosed with the vapor of the male attracting agent, the mating responses of the males become totally confused and they will not mate even if females are in the vicinity. It has therefore been found advantageous to distribute the attractant compositions in the form of water insoluble micro capsules which may be prepared by methods well known in the art. These micro capsules may either be scattered or sprayed upon the leaves of areas immediately adjacent to the area to be protected in combination with a substantially water insoluble adhesive material which is not harmful to the surrounding vegitation. The advantage of spraying the material and adhering it to adjacent vegitation it that it permits a better flow of air past the material than would be the case if mere scattering were employed.

In connection with the encapsulation disclosure contained herein, the expression "internal phase" will be employed with reference to those materials which are encapsulated, whereas the term "external phase" is used with reference to the cell wall material, viz., the material which constitutes the capsule wall of the encapsulating material. A recommended encapsulation procedure for encapsulating can be found in U.S. Pat. No. 3,265,629. Additional encapsulation procedures, both chemical and mechanical, which can be used to encapsulate various materials of this invention can be found in "Microencapsulation" by Anderson et al. (Harvard M.B.A. Candidates report), published by Management Reports, Boston, Mass. (1963), the disclosure of which are both incorporated herein by reference.

In similar manner a wide variety of external phase (cell wall) materials can be used to encapsulate the above-mentioned and other components. Suitable exemplary encapsulating materials which can be used in accordance with this invention include, but are not limited to, the following: polyvinylidene chloride, polyethlene, ethyl cellulose, nitrocellulose, polystyrene, shellac, polyvinylalcohol, ureaformaldehyde and other aminoplast condensates, phenol-formaldehyde and other phenolic condensates, etc. The disruptive dose may vary depending on mode of administration as well as climatic conditions but will be about 1 – 1000 mg/m$^2$.

EXAMPLE I

Preparation of cis-9-tetradecenal

Chromium trioxide (0.56 g. 5.6 mM) is added to a stirred solution of pyridine (0.90 g. 11.4 mM) in methylene chloride (14 ml). The flask is stoppered with a Drieritefilled tube. The deep red solution is stirred for approximately fifteen minutes at room temperature after which a solution of cis-9-tetradecen-1-ol (0.9 mM) in a small amount of methylene chloride (approximately 0.2 ml) is added rapidly and the mixture stirred for another 15 minutes. The product is recovered by decantation from the tarry precipitate, concentrated in vacuo, and the residue extracted with redistilled petroleum ether (Skelly B). This extract is washed successively with dilute aqueous hydrochloric acid (approximately 1%), brine, dilute aqueous sodium bicarbonate (approximately 5%), and brine (until neutral), then filtered through anhydrous magnesium sulfate and evaporated in vacuo to yield 0.17 g. G.c. analysis showed the product contained cis-9-tetradecen-1-ol in approximately 1:9 ratio to the aldehyde, so the product was chromatographed on Florisil (2.4 cm o.d. × 30 cm; packed up to 25 cm) using redistilled benzene (15 ml fractions). Fractions 4 – 7 are combined. Final yield of alcohol-free cis-9-tetradecenal is 60 mg. In accordance with the foregoing procedure but starting with cis-11-hexadecenal in place of cis-9-tetradecenal, there is obtained crude cis-5-hexadecenal (0.19 g.) and alcohol-free cis-11-hexadecenal (0.10 g.).

EXAMPLE II

Isomerically pure cis-aldehydes

Isomerically pure cis-9-tetradecenal and cis-11-hexadecenal prepared by converting cis-9tetradecenol and cis-11-hexadecenol to the corresponding acetates cis-9-tetradecenyl acetate and cis-11-hexadecenyl acetate by conventional methods and subjecting these acetates to preparative thin layer chromatography Ag NO$_3$ - impregnated silica gel G (15 g. on 35 g., respectively) using benzene as the eluant and 2', 7'-dichlorofluorescein as the visualizing spray. The recovered cis-acetates are saponified by the conventional procedure (refluxing 5% Na OH in 85–90% ethanol) and oxidized as described hereinabove.

Preparation of starting materials

Cis-9-tetradecenol acetate is prepared in accordance with the procedures set forth in J. Med. Chem. 11 371 (1968) the disclosure of which is incorporated herein by reference. The synthesis requires reaction of 8-chloro-1-octanol with dihydropyran to give the 8-chloro-1-octanol THP derivative which is reacted with lithium acetylide to yield dec-9-yn-1-ol-THP. Treatment with lithium amide and butyl bromide gives the tetradec-9-yn-1-ol-THP which is reduced suitably with hydrogen on calcium carbonate in the presence of quinoline to yield the cis-9-tetradecen-1-ol THP which is directly converted to the acetate which in turn in saponified with alkali as set forth hereinabove to yield the appropriate alcohol.

In accordance with the above procedure, but starting with 10-chloro-1-decanol in place of 8-chloro-1-octanol, there is obtained cis-11-hexadecenol.

We claim:
1. An insect attractant for males of the species virescens comprising from 200 to 2 parts of cis-11-hexadecenal per 1 part of cis-9-tetradecenal.
2. A composition of Claim 1 comprising 3 parts of cis-11-hexadecenal per 1 part of cis-9-tetradecenal.
3. A method of trapping males of the species of *H. virescens* by charging insect traps with from 1 – 10,000 μg per trap of a composition of Claim 1 and placing said trap in a location infested by said species.
4. A method of disorienting males of the species *H. virescens* by broadcasting, throughout a predetermined location infested with said species, from between 0.1 and 1,000 mg./sq. meter of a composition of Claim 1 in sustained release micro capsules.
5. A method of trapping males of the species *H. zea* by charging insect traps with from 1 – 10,000 μg per trap of a composition comprising cis-11-hexadecenal and placing said trap in a location infested by said species.
6. A method of disorienting males of the species *H. zea* by broadcasting, throughout a predetermined location infested with said species, from between 0.1 and 1,000 mg./sq. meter of a composition comprising cis-11-hexadecenal in sustained release micro capsules.

* * * * *